United States Patent
Sajitz et al.

(10) Patent No.: US 8,907,118 B2
(45) Date of Patent: *Dec. 9, 2014

(54) METHOD FOR PRODUCING ACYLOXY BENZOIC ACIDS

(75) Inventors: Melanie Sajitz, Plettenberg (DE); Gerd Reinhardt, Kelkheim (DE); Isabel Scheffer, Frankfurt (DE); Werner Janitschek, Heistenbach (DE); Ina Herrgen, Ruesselsheim (DE)

(73) Assignee: Clariant International Ltd., Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/816,686

(22) PCT Filed: Aug. 6, 2011

(86) PCT No.: PCT/EP2011/003957
§ 371 (c)(1),
(2), (4) Date: Mar. 20, 2013

(87) PCT Pub. No.: WO2012/019743
PCT Pub. Date: Feb. 16, 2012

(65) Prior Publication Data
US 2013/0217911 A1    Aug. 22, 2013

(30) Foreign Application Priority Data

Aug. 13, 2010   (DE) .................. 10 2010 034 243

(51) Int. Cl.
C07C 67/14   (2006.01)
(52) U.S. Cl.
CPC .................................... *C07C 67/14* (2013.01)
USPC ........................................................... 560/98
(58) Field of Classification Search
None
See application file for complete search history.

(56) References Cited

U.S. PATENT DOCUMENTS

| 5,380,917 A | 1/1995 | Kottwitz et al. |
| 5,891,838 A * | 4/1999 | Angell et al. ................. 510/312 |
| 2005/0230660 A1 * | 10/2005 | Parker et al. ............... 252/299.2 |

FOREIGN PATENT DOCUMENTS

| EP | 0164786 A2 | 12/1985 |
| EP | 0294073 A1 | 12/1988 |
| JP | 2000086581 | 3/2000 |
| WO | 9215556 A1 | 9/1992 |

OTHER PUBLICATIONS

Sivasamy et al. ChemSusChem 2009, 2, 278-300.*

* cited by examiner

*Primary Examiner* — Brandon Fetterolf
*Assistant Examiner* — Ana Z Muresan
(74) *Attorney, Agent, or Firm* — Michael W. Ferrell

(57) ABSTRACT

The invention relates to a method for producing acyloxy benzoic acids of the formula (I), in which $R^1$ is a linear or branched saturated alkyl group with 6 to 30 carbon atoms, a linear or branched mono- or polyunsaturated alkenyl group with 6 to 30 carbon atoms, or an aryl group with 6 to 30 carbon atoms. The acyloxy benzoic acids of the formula (I) are produced from para-hydroxy benzoic acid and a corresponding carboxylic acid halide in the presence of an alkali hydroxide.

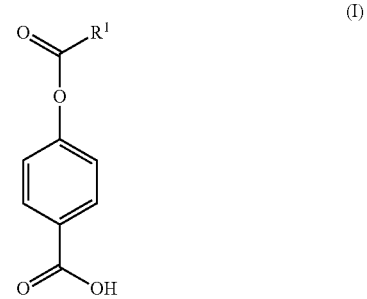

20 Claims, No Drawings

METHOD FOR PRODUCING ACYLOXY BENZOIC ACIDS

The present invention relates to a process for preparing acyloxybenzoic acids starting from para-hydroxybenzoic acid and carboxylic halides.

Inorganic peroxygen compounds, especially hydrogen peroxide and solid peroxygen compounds which dissolve in water and in so doing release hydrogen peroxide, such as sodium perborate and sodium percarbonate, have long been used as oxidizing agents for purposes of disinfection and bleaching. The oxidation effect of these substances in dilute solutions is heavily dependent on the temperature. For example, with $H_2O_2$ or perborate in alkaline bleaching liquors, sufficiently rapid bleaching of soiled textiles is obtained only at temperatures above about 80° C.

At lower temperatures, the oxidation effect of the inorganic peroxygen compounds can be improved by addition of what are called bleach activators. Numerous proposals to this have been elaborated in the past, especially from the classes of the N- or O-acyl compounds.

In recent years, the compounds according to formula (Ia)

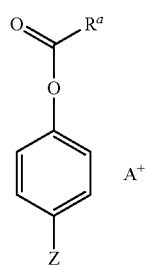

$Z = CO_2^-, SO_3^-$ in which the radical $R^a$ in particular is a linear or branched, saturated alkyl group having 6 to 22 carbon atoms or is a linear or branched, singly or multiply unsaturated alkenyl group having 6 to 22 carbon atoms, and $A^+$ in particular is an alkali metal or alkaline earth metal ion, and preferably a sodium ion, have been of interest as activators for inorganic peroxy compounds. Of particular interest was the use of these compounds as bleaching agents or as a peroxy acid precursor.

These peroxy acid precursors react in aqueous solution with the inorganic peroxy compounds such as sodium percarbonate or sodium perborate which are present in the laundry detergent, and form organic peroxy acids which bleach much more effectively at low temperatures (<70° C.) than do the inorganic peroxy compounds.

Of particular note are acyloxybenzoic acids according to the formula (Ib)

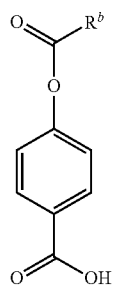

in which $R^b$ in particular is a linear or branched, saturated alkyl group having 6 to 30 carbon atoms, a linear or branched, singly or multiply unsaturated alkenyl group having 6 to 30 carbon atoms, or an aryl group having 6 to 30 carbon atoms, and also the salts thereof, these being, in particular, alkali metal salts or alkaline earth metal salts, since not only are they very good bleach activators, but they are also found, advantageously, not to be skin-sensitizing.

Not only the phenol ester sulfonates but also the acyloxybenzoic acids and salts thereof are obtainable in principle, for example, through reaction of carboxylic chlorides such as, for example, alkyl acid chloride with phenolsulfonate or para-hydroxybenzoic acid by the Schotten-Baumann reaction. Examples of this are found inter alia in EP 0 294 073, EP 0 164 786 or WO 92/15556.

The acyloxybenzoic acids can be prepared from acid chlorides and para-hydroxybenzoic acid even at high temperatures >30° C. (JP 4194688). A disadvantage of the process, however, is the formation of secondary components such as dimers and trimers of the para-hydroxybenzoic acid and/or esters of the dimeric para-hydroxybenzoic acid. The incidence of such secondary components, which cannot be separated off, is extremely undesirable in laundry detergents.

U.S. Pat. No. 5,891,838 discloses a process for preparing para-decanoyloxybenzoic acid that provides diethyl ether and water as a solvent mixture. The yield of 40%, however, is unsatisfactory, and the industrial handling of diethyl ether is undesirable on workplace safety grounds.

It was an object of the present invention to provide a process for preparing long-chain or aromatic acyloxybenzoic acids that can be carried out on an industrial scale and leads in high yields to the acyloxybenzoic acids, the acyloxybenzoic acids being suitable, in terms of composition and quality, for use in laundry and other detergents.

It has now been found that this object is achieved by a process for preparing acyloxybenzoic acids of the formula (I)

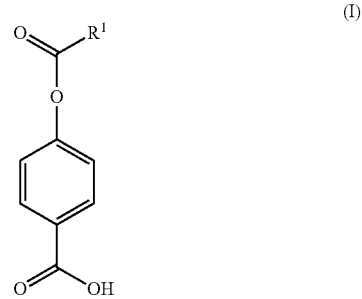

in which
$R^1$ is a linear or branched, saturated alkyl group having 6 to 30 carbon atoms, a linear or branched, singly or multiply unsaturated alkenyl group having 6 to 30 carbon atoms, or an aryl group having 6 to 30 carbon atoms,
which comprises
a) admixing para-hydroxybenzoic acid, in a solvent mixture comprising water and one or more organic solvents, with an alkali metal hydroxide, in an alkali metal hydroxide:para-hydroxybenzoic acid molar ratio ≥1.9:1 and only thereafter adding a carboxylic halide of formula $R^1$COHal, in which $R^1$ possesses the definition indicated above and Hal is a halide, at a temperature 25° C., and carrying out reaction, b) adjusting the reaction mixture after step a), at a temperature ≤25° C., to a pH of 6 to 8.5 by addition of acid, if the pH at the end of step a) is not already within this range,
c) after step b), where that step takes place, and otherwise after step a), heating the reaction mixture to a temperature of 35 to 80° C. and thereafter adjusting it to a pH of 1 to 4 by addition of acid, and
e) adding the entire amount of alkali metal hydroxide in step a) before the addition of the carboxylic halide to the reaction mixture, and otherwise adding no further base in the process.

The invention accordingly provides a process for preparing acyloxybenzoic acids of the formula (I)

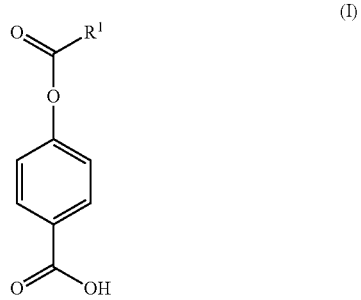

(I)

in which
R¹ is a linear or branched, saturated alkyl group having 6 to 30, preferably 7 to 15 and more preferably 7 to 11 carbon atoms, a linear or branched, singly or multiply unsaturated alkenyl group having 6 to 30, preferably 7 to 15 and more preferably 7 to 11 carbon atoms, or an aryl group having 6 to 30 carbon atoms,
which comprises
a) admixing para-hydroxybenzoic acid, in a solvent mixture comprising water and one or more organic solvents, with an alkali metal hydroxide, in an alkali metal hydroxide:para-hydroxybenzoic acid molar ratio ≥1.9:1 and only thereafter adding a carboxylic halide of formula R¹COHal, in which R¹ possesses the definition indicated above and Hal is a halide, at a temperature 25° C., preferably at 0 to 25° C. and more preferably at 0 to 15° C., and carrying out reaction,
b) adjusting the reaction mixture after step a), at a temperature ≤25° C., preferably at 0 to 25° C. and more preferably at 0 to 15° C., to a pH of 6 to 8.5 and preferably 6 to 8 by addition of acid, if the pH at the end of step a) is not already within this range,
c) after step b), where that step takes place, and otherwise after step a), heating the reaction mixture to a temperature of 35 to 80° C., preferably from 50 to 70° C., and thereafter adjusting it to a pH of 1 to 4 by addition of acid, preferably HCl, and
e) adding the entire amount of alkali metal hydroxide in step a) before the addition of the carboxylic halide to the reaction mixture, and otherwise adding no further base in the process.

In step a) of the process of the invention, both the addition and also the reaction of the carboxylic halide take place at a temperature 25° C., preferably at 0 to 25° C., and more preferably at 0 to 15° C.

The process of the invention possesses the advantage that the acyloxybenzoic acids of the formula (I) can be easily isolated from the reaction mixture by filtration. The acyloxybenzoic acids obtained by the process of the invention are white to cream in color and can be used in the form of powder or granules for the manufacture of laundry and other detergents. A particular advantage is that the acyloxybenzoic acids obtained by the process of the invention have a very high purity and contain secondary components such as dimers or trimers of the para-hydroxybenzoic acid preferably in an amount <1.0% by weight. In contrast to acyloxybenzoic acids from other processes, which generally contain byproducts, the acyloxybenzoic acids from the process of the invention, on account of their high purity, are especially suitable for use in laundry and other detergents.

The process of the invention possesses the advantage, furthermore, that there is no substantial precipitation during the addition of the carboxylic halide in step a) of the process of the invention.

In step a) of the process of the invention, the entire amount of alkali metal hydroxide is added prior to the addition of the carboxylic halide to the reaction mixture, and, otherwise, no further base is added in the process. The advantage of this procedure is, for example, that there is no need for pH monitoring during the reaction in step a), and the process can therefore be implemented simply.

Provided the pH lowers during step a) to an extent such that at the end of step a) it is from 6 to 8.5 and preferably from 6 to 8, step b) of the process of the invention is omitted.

Preferred carboxylic halides of formula R¹COHal are those in which Hal is Cl or Br. Particularly preferred carboxylic halides of the formula R¹COHal are the carboxylic chlorides according to the formula (II)

(II)

Where the radical R¹ represents an aryl group, it is preferably a phenyl group or else a phenyl group substituted by 1 to 3 methyl groups. Among these substituted phenyl groups, the group —C₄H₆—CH₃ is preferred in turn. Among the aryl groups, however, the (unsubstituted) phenyl group is particularly preferred.

Preferably, though, the radical R¹ is an alkyl or alkenyl group. Examples of carboxylic acids R¹—COOH which form the base for the carboxylic halides R¹—COHal are heptanoic acid, octanoic acid, methyloctanoic acid, nonanoic acid, 3,3,5-isononanoic acid, decanoic acid, undecanoic acid, undecenoic acid, dodecanoic acid, tetradecanoic acid, hydrogenated tallow fatty acid, and octadecanoic acid.

More preferably the radical R¹ is an alkyl group. With more particular preference, the carboxylic acids R¹—COOH on which the carboxylic halides are based are selected from the group consisting of octanoic acid, nonanoic acid, 3,3,5-isononanoic acid, decanoic acid, and dodecanoic acid. Among these, nonanoic acid and decanoic acid are preferred in turn.

The process of the invention is preferably performed such that after step c) the reaction mixture is cooled to a temperature <35° C., more preferably <30° C., with more particular preference from 0 to 30° C., and extraordinarily preferably from 5 to 25° C. (step d)). In this way it is possible in particular to achieve a boost in yield.

The alkali metal hydroxide added in the acylation reaction in step a) of the process of the invention has the function of allowing reaction through formation of the phenolate. The alkali metal hydroxide used in step a) is preferably KOH or NaOH, and more preferably it is KOH.

The one or more organic solvents used in step a) of the process of the invention are preferably selected from the group consisting of linear or branched alcohols and open-chain or cyclic ethers.

More preferably, the one or more organic solvents used in step a) of the process of the invention possess from 1 to 10 carbon atoms and preferably from 1 to 6 carbon atoms.

In one especially preferred embodiment of the invention, the alcohols used as organic solvents are selected from secondary and tertiary alcohols having 3 to 6 carbon atoms.

In another especially preferred embodiment of the invention, the one or more organic solvents used in step a) of the process of the invention possess from 1 to 5 carbon atoms. Of these, in turn, preference is given to the one or more organic solvents used in step a) being selected from the group consisting of methanol, ethanol, n-propanol, isopropanol, n-butanol, isobutanol, tert-butanol, diethyl ether, tetrahydrofuran, dioxane, and mixtures thereof.

Very preferably the organic solvent used in step a) of the process of the invention is isopropanol.

The acid used in step b) (provided said step b) takes place) and in step c) of the process of the invention preferably possesses a pKa value of less than or equal to 4.0. This acid more preferably is $H_2SO_4$ or HCl, and especially preferably HCl.

The weight ratio of water to the one or more organic solvents in step a) is preferably from 5:1 to 1:5 and more preferably from 3:1 to 1:2.

The weight ratio of water to para-hydroxybenzoic acid in step a) is preferably from 2:1 to 10:1 and more preferably from 2:1 to 6:1.

The molar ratio of the carboxylic halide of the formula $R^1COHal$ to para-hydroxybenzoic acid is preferably from 0.75:1 to 1.5:1, more preferably from 0.9:1 to 1.1:1, and especially preferably 1:1.

The alkali metal hydroxide: para-hydroxybenzoic acid molar ratio is preferably from 1.9:1 to 3:1, more preferably from 2:1 to 2.5:1, and especially preferably from 2:1 to 2.2:1.

The procedure for isolating and purifying the acyloxybenzoic acids of the formula (I) that are prepared by the process of the invention is preferably as follows: The reaction mixture is filtered by conventional separation methods (filter apparatus), preferably at room temperature, and the residue is washed with water until there is no longer any salt present. Filtration takes place preferably after step d). The acyloxybenzoic acid formed is obtained in high yields in the form of a white powder, which can be dried by conventional methods.

The end product contains traces at most of the carboxylic acid $R^1$—COOH. Unreacted para-hydroxybenzoic acid and salts such as potassium chloride, for example, can be removed completely from the filter cake by washing with water.

The present invention further provides an acyloxybenzoic acid obtainable by the process of the invention.

The product of the process of the invention can be used advantageously as an activator for hydrogen peroxide.

The present invention accordingly further provides the use of an acyloxybenzoic acid obtainable by the process of the invention as an activator for hydrogen peroxide.

In their action as bleach activators, the acyloxybenzoic acids obtainable by the process of the invention are significantly more effective than acyloxybenzoic acids prepared by conventional processes. With the acyloxybenzoic acids obtainable by the process of the invention, the release of peracid takes place significantly earlier than in the case of acyloxybenzoic acids prepared by conventional processes.

The acyloxybenzoic acids obtainable by the process of the invention can be used as persalt activators in liquid or powder laundry and other detergents such as heavy-duty laundry powder detergents, scouring salts, or machine powder dishwash detergents. In order to increase the shelf life in these formulations, the acids may be converted into a granular form, as is known to the skilled person. As a result of the activation, it is possible, in laundry and other detergents, for example, to enhance the bleaching performance of the inorganic peroxy compounds/hydrogen peroxide or, in disinfectants, to boost the disinfection performance.

The examples below are intended to illustrate the invention, though without confining it to them.

EXAMPLES

Example 1

Synthesis of Para-decanoyloxybenzoic Acid (DOBA)

138.1 g (1.0 mol) of para-hydroxybenzoic acid were first dissolved in 400 ml of water and 600 ml of isopropanol and this solution was admixed at 0 to 5° C. with 235.7 g of KOH solution (50% strength by weight aqueous solution, 2.1 mol). The resulting pH was 14. Metered into this solution over the course of three hours, then, at 0 to 5° C., were 190.7 g (1.0 mol) of decanoyl chloride, and the batch was stirred for 30 minutes at 0 to 5° C. thereafter. At the end of the after-stirring, the pH of the reaction mixture was 9.7. The reaction mixture was subsequently adjusted to a pH of 8 at 0 to 5° C. using 25.6 g of HCl solution (32% strength by weight aqueous solution), and the complete solution was heated to 55 to 60° C. and then adjusted to a pH of 1.5 to 3 using 100 g of HCl solution (32% strength by weight aqueous solution). The reaction mixture was cooled to 20 to 25° C. and the solid was filtered off on a suction filter and washed ten times with 150 ml of water. The yield after drying under reduced pressure at 100° C. was 268.3 g (91.8% of theory). According to HPLC and NMR measurement, the product was free from decanoic acid and from unreacted para-hydroxybenzoic acid. The purity of the product is >99.9% by weight.

Example 2

Synthesis of Para-decanoyloxybenzoic Acid (DOBA)

138.1 g (1.0 mol) of para-hydroxybenzoic acid were first dissolved in 400 ml of water and 600 ml of isopropanol and this solution was admixed at 20 to 25° C. with 235.7 g of KOH solution (50% strength by weight aqueous solution, 2.1 mol). The resulting pH was 14. Metered into this solution over the course of three hours, then, at 20 to 25° C., were 190.7 g (1.0 mol) of decanoyl chloride, and the batch was stirred for 30 minutes at 20 to 25° C. thereafter. The complete solution was subsequently heated to 55 to 60° C. and then adjusted to a pH of 1.5 to 3 using 124.7 g of HCl solution (32% strength by weight aqueous solution). The reaction mixture was cooled to 20 to 25° C. and the solid was filtered off on a suction filter and washed ten times with 150 ml of water. The yield after drying under reduced pressure at 100° C. was 237.5 g (81.2% of theory). According to HPLC and NMR measurement, the product was free from decanoic acid and from unreacted para-hydroxybenzoic acid. The purity of the product is >99.9% by weight.

Example 3

Synthesis of Para-decanoyloxybenzoic Acid (DOBA)

138.1 g (1.0 mol) of para-hydroxybenzoic acid were first dissolved in 400 ml of water and 600 ml of isopropanol and this solution was admixed at 10 to 15° C. with 235.7 g of KOH solution (50% strength by weight aqueous solution, 2.1 mol). The resulting pH was 14. Metered into this solution over the course of three hours, then, at 10 to 15° C., were 190.7 g (1.0 mol) of decanoyl chloride, and the batch was stirred for 30 minutes at 10 to 15° C. thereafter. At the end of the after-stirring, the pH of the reaction mixture was 8.7. The reaction mixture was subsequently adjusted to a pH of 8 at 10 to 15° C. using 10.4 g of HCl solution (32% strength by weight aqueous solution), and the complete solution was heated to 55 to 60° C. and then adjusted to a pH of 1.5 to 3 using 115 g of HCl solution (32% strength by weight aqueous solution). The reaction mixture was cooled to 20 to 25° C. and the solid was filtered off on a suction filter and washed ten times with 150 ml of water. The yield after drying under reduced pressure at 100° C. was 257.0 g (87.9% of theory). According to HPLC and NMR measurement, the product was free from decanoic acid and from unreacted para-hydroxybenzoic acid. The purity of the product is >99.9% by weight.

Example 4

Synthesis of Para-decanoyloxybenzoic Acid (DOBA)

69.1 g (0.5 mol) of para-hydroxybenzoic acid were first dissolved in 200 ml of water and 300 ml of isopropanol and this solution was admixed at 10 to 15° C. with 127.5 g of NaOH solution (32% strength by weight aqueous solution, 1.02 mol). The resulting pH was 13.7. Metered into this solution over the course of three hours, then, at 10 to 55° C., were 95.4 g (0.5 mol) of decanoyl chloride, and the batch was stirred for 30 minutes at 10 to 15° C. thereafter. The complete solution was subsequently heated to 55 to 60° C. and then adjusted to a pH of 1.5 to 3 using 60.0 g of HCl solution (32% strength by weight aqueous solution). The reaction mixture was cooled to 20 to 25° C. and the solid was filtered off on a suction filter and washed ten times with 75 ml of water. The yield after drying under reduced pressure at 100° C. was 124.8 g (85.4% of theory). According to HPLC and NMR measurement, the product was free from decanoic acid and from unreacted para-hydroxybenzoic acid. The purity of the product is >99.9% by weight.

Comparative Example 1

Synthesis of Para-decanoyloxybenzoic Acid (DOBA)

116.3 g (0.61 mol) of decanoyl chloride were heated to 125° C. in 300 ml of xylene, and 69.1 g (0.5 mol) of 4-hydroxybenzoic acid were introduced in portions over the course of six hours. The batch was subsequently stirred at 125° C. for one hour, cooled to room temperature, and filtered with suction, and the solid product was washed three times with 45 ml of xylene. The yield after drying under reduced pressure at 100° C. was 108.4 g (74% of theory). According to HPLC and NMR measurement, the product was free from decanoic acid and from unreacted para-hydroxybenzoic acid, but contained 0.4% by weight of byproducts such as dimers and trimers of the para-hydroxybenzoic acid.

Comparative Example 2

Synthesis of Para-decanoyloxybenzoic Acid (DOBA) According to U.S. Pat. No. 5,891,838, Example XV DOBA was prepared according to example XV of U.S. Pat. No. 5,891,838. After the filtration of the product (which had a greasy consistency, with the disadvantageous consequence of making the filtration last a very long time), the work-up procedure was as follows: the residue from the filtration was washed with water a number of times, and the product was dried under reduced pressure at 100° C. The yield was 90.6 g. According to HPLC and NMR measurement, the product contained 10.9% by weight of decanoic acid, 30.4% by weight of DOBA and 41% by weight of para-hydroxybenzoic acid. The product was subsequently recrystallized for purification, as in U.S. Pat. No. 5,891,838, and employed for the measurement of the peracid kinetics (see example 5 below).

Example 5

Determining the Peracid Kinetics of Para-decanoyloxybenzoic Acid (DOBA) from Inventive Example 1 and from Comparative Examples 1 and 2

The peracid kinetics were determined by means of iodometric titration using sodium thiosulfate solution.

The basis for the measurement is that para-decanoyloxybenzoic acid (DOBA) and hydrogen peroxide react in aqueous solution to form perdecanoic acid and para-hydroxybenzoic acid (if inorganic peroxides are used, they react in aqueous solution to form hydrogen peroxide). The reaction between DOBA and hydrogen peroxide takes place rapidly and quantitatively in dilute aqueous solution at a pH of 10 to 11 and at 20° C. The perdecanoic acid formed can then be determined by iodometry, along with the hydrogen peroxide which is present in excess. The perdecanoic acid is substantially more reactive than hydrogen peroxide and, in a weakly acidic medium and at a low temperature, it undergoes immediate oxidation with added iodide $I^-$ (added in the form of potassium iodide, for example) to form iodine $I_2$. The iodine formed can then be titrated with sodium thiosulfate. The corresponding amount of perdecanoic acid can then be calculated from the amount of iodine found.

The specific procedure was as follows:

1 liter of deionized water at 20° C. was introduced in a 2 liter glass beaker and stirred. 1.5 g of sodium percarbonate and 8 g of a standard laundry detergent ("IEC 60 456 type A*" from WFK Testgewebe GmbH) were added and subjected to preliminary dissolution for 2 minutes. Then 0.25 g of the DOBA under analysis was added. After 3 minutes, 50 ml were pipetted off and introduced into a 250 ml glass beaker, onto 50 g of ice made from deionized water and 10 ml of acetic acid (20% strength by weight aqueous solution). Then 5 ml of aqueous potassium iodide solution (10% strength by weight aqueous solution) were added, and titration took place with sodium thiosulfate solution (0.01 molar aqueous solution).

Titration was carried out using a Titrino DMS 716 or Basic 794 (Metrohm) with a 50-way changeover unit and keyboard, and also a Ti Stand 727 (Metrohm) with drawn burette tip, stirring rod, and combined platinum electrode.

The next samples were taken after particular times following the addition of DOBA, and were titrated as described above. As sampling time goes on, the amount of perdecanoic acid approaches a maximum value, and then remains constant in the case of samples taken later. This maximum value for the amount of perdecanoic acid is set at 100%. The amounts of perdecanoic acid for the other samples are then expressed in relation to this 100%.

The results of the determination of the peracid kinetics, i.e., the results of determination of the amount of perdecanoic acid as a function of time, are shown in table 1.

TABLE 1

Results of the determination of the peracid kinetics of para-decanoyloxybenzoic acid (DOBA)

Amount of perdecanoic acid [%]

| Time [min] | Use of DOBA from inventive example 1 | Use of DOBA from comparative example 1 | Use of DOBA from comparative example 2 |
|---|---|---|---|
| 3 | 90.6 | 66.85 | 82.04 |
| 6 | 94.9 | 82.92 | 84.28 |
| 9 | 99.1 | 87.98 | 88.00 |
| 12 | 100.00 | 92.91 | 93.38 |
| 15 |  | 96.44 | 94.32 |
| 18 |  | 100.00 | 100.00 |

The results in table 1 describe the release of active ingredient from para-decanoyloxybenzoic acid (DOBA), i.e., here, the release of perdecanoic acid, as a function of time. They reveal that the active ingredient is released more quickly from the DOBA produced according to inventive example 1 than is the active ingredient from the DOBAs produced according to comparative examples 1 and 2. Specifically, it is apparent from the results from table 1 that the DOBA produced according to comparative examples 1 and 2 has generated 100% of the perdecanoic acid only after 18 minutes, whereas the DOBA produced according to inventive example 1 reaches this level after just 12 minutes.

With a view to the use of the resultant acyloxybenzoic acids of the formula (I) in laundry detergents, therefore, the process of the invention represents a significant improvement.

Example 6

Synthesis of Para-decanoyloxybenzoic Acid (DOBA)

The process was as in example 1, but at a batch size of 5 mol the metering time of the decanoyl chloride was changed from three hours to 20 minutes. The yield is 1242.62 kg (85%). The purity of the product is >99.9% by weight.

The $d_{10}$ value of the particles is 10.358 μm, the $d_{50}$ value is 52.548 μm, and the $d_{90}$ value is 140.059 μm.

Example 7

Synthesis of Para-benzoyloxybenzoic Acid (BOBA)

138.1 g (1.0 mol) of para-hydroxybenzoic acid were first dissolved in 400 ml of water and 600 ml of isopropanol and this solution was admixed at 0 to 5° C. with 235.7 g of KOH solution (50% strength by weight aqueous solution, 2.1 mol). The resulting pH was 14. Metered into this solution over the course of one hour, then, at 0 to 5° C., were 140.4 g (1.0 mol) of benzoyl chloride, and the batch was stirred for 30 minutes at 0 to 5° C. thereafter. At the end of the after-stirring, the pH of the reaction mixture was 9.3. The reaction mixture was subsequently adjusted to a pH of 8 at 0 to 5° C. using 25.0 g of HCl solution (32% strength by weight aqueous solution), and the complete solution was heated to 55 to 60° C. and then adjusted to a pH of 1.5 to 3 using 100 g of HCl solution (32% strength by weight aqueous solution). The reaction mixture was cooled to 20 to 25° C. and the solid was filtered off on a suction filter and washed ten times with 150 ml of water. The yield after drying under reduced pressure at 100° C. was 220.5 g (91.0% of theory). According to HPLC and NMR measurement, the product was free from benzoic acid and from unreacted para-hydroxybenzoic acid. The purity of the product is >99.9% by weight.

Example 8

Synthesis of Para-nonanoyloxybenzoic Acid (NOBA)

138.1 g (1.0 mol) of para-hydroxybenzoic acid were first dissolved in 500 ml of water and 500 ml of isopropanol and this solution was admixed at 0 to 5° C. with 230.0 g of KOH solution (50% strength by weight aqueous solution, 2.05 mol). The resulting pH was 13.5. Metered into this solution over the course of one hour, then, at 0 to 5° C., were 176.6 g (1.0 mol) of nonanoyl chloride, and the batch was stirred for 30 minutes at 0 to 5° C. thereafter. At the end of the after-stirring, the pH of the reaction mixture was 9.0. The reaction mixture was subsequently adjusted to a pH of 8 at 0 to 5° C. using 25.0 g of HCl solution (32% strength by weight aqueous solution), and the complete solution was heated to 55 to 60° C. and then adjusted to a pH of 1.5 to 3 using 100 g of HCl solution (32% strength by weight aqueous solution). The reaction mixture was cooled to 20 to 25° C. and the solid was filtered off on a suction filter and washed ten times with 150 ml of water. The yield after drying under reduced pressure at 100° C. was 255.95 g (92.0% of theory). According to HPLC and NMR measurement, the product was free from nonanoic acid and from unreacted para-hydroxybenzoic acid. The purity of the product is >99.9% by weight.

Example 9

Synthesis of Para-decanoyloxybenzoic Acid (DOBA)

172.7 g (1.25 mol) of para-hydroxybenzoic acid were first dissolved in 400 ml of water and 600 ml of isopropanol and this solution was admixed at 10 to 15° C. with 287.3 g of KOH solution (50% strength by weight aqueous solution, 2.56 mol). The resulting pH was 14. Metered into this solution over the course of two hours, then, at 10 to 15° C., were 238.4 g (1.25 mol) of decanoyl chloride, and the batch was stirred for 15 minutes at 10 to 15° C. thereafter. At the end of the after-stirring, the pH of the reaction mixture was 9.7. The reaction mixture was subsequently admixed at 10 to 15° C. with 31.3 g of HCl solution (32% strength by weight aqueous solution), and the complete solution was heated to 55 to 60° C. and then adjusted to a pH of 1.5 to 3 using 125 g of HCl solution (32% strength by weight aqueous solution). The reaction mixture was cooled to 20 to 25° C. and the solid was filtered off on a suction filter and washed ten times with 150 ml of water. The yield after drying under reduced pressure at 100° C. was 321.0 g (87.8% of theory). According to HPLC and NMR measurement, the product was free from decanoic acid and from unreacted para-hydroxybenzoic acid. The purity of the product is >99.9% by weight.

Example 10

Synthesis of Para-decanoyloxybenzoic Acid (DOBA)

165.7 g (1.2 mol) of para-hydroxybenzoic acid were first dissolved in 400 ml of water and 600 ml of isopropanol and this solution was admixed at 10 to 15° C. with 276.1 g of KOH solution (50% strength by weight aqueous solution, 2.46 mol). The resulting pH was 14. Metered into this solution over the course of two hours, then, at 10 to 15° C., were 228.8 g (1.2 mol) of decanoyl chloride, and the batch was stirred for 15 minutes at 10 to 15° C. thereafter. At the end of the after-stirring, the pH of the reaction mixture was 9.5. The reaction mixture was subsequently admixed at 10 to 15° C. with 30 g of HCl solution (32% strength by weight aqueous solution), and the complete solution was heated to 55 to 60° C. and then adjusted to a pH of 1.5 to 3 using 120 g of HCl solution (32% strength by weight aqueous solution). The reaction mixture was cooled to 20 to 25° C. and the solid was filtered off on a suction filter and washed ten times with 150 ml of water. The yield after drying under reduced pressure at 100° C. was 314.4 g (89.6% of theory). According to HPLC and NMR measurement, the product was free from decanoic acid and from unreacted para-hydroxybenzoic acid. The purity of the product is >99.9% by weight.

Example 11

Synthesis of Para-decanoyloxybenzoic Acid (DOBA)

158.8 g (1.15 mol) of para-hydroxybenzoic acid were first dissolved in 400 ml of water and 600 ml of isopropanol and this solution was admixed at 10 to 15° C. with 264.8 g of KOH solution (50% strength by weight aqueous solution, 2.36 mol). The resulting pH was 14. Metered into this solution over the course of two hours, then, at 10 to 15° C., were 219.4 g (1.15 mol) of decanoyl chloride, and the batch was stirred for 15 minutes at 10 to 15° C. thereafter. At the end of the after-stirring, the pH of the reaction mixture was 9.1. The reaction mixture was subsequently admixed at 10 to 15° C. with 28.8 g of HCl solution (32% strength by weight aqueous solution), and the complete solution was heated to 55 to 60° C. and then adjusted to a pH of 1.5 to 3 using 115 g of HCl solution (32% strength by weight aqueous solution). The reaction mixture was cooled to 20 to 25° C. and the solid was filtered off on a suction filter and washed ten times with 150 ml of water. The yield after drying under reduced pressure at 100° C. was 296.1 g (88.1% of theory). According to HPLC and NMR measurement, the product was free from decanoic acid and from unreacted para-hydroxybenzoic acid. The purity of the product is >99.9% by weight.

Example 12

Synthesis of Para-decanoyloxybenzoic Acid (DOBA)

138.1 g (1 mol) of para-hydroxybenzoic acid were first dissolved in 400 ml of water and 600 ml of isopropanol and this solution was admixed at 0 to 5° C. with 235.7 g of KOH solution (50% strength by weight aqueous solution, 2.1 mol). The resulting pH was 14. Metered into this solution over the course of 15 minutes, then, at 5 to 25° C., without counter-cooling, were 190.7 g (1 mol) of decanoyl chloride, and the batch was stirred for 15 minutes thereafter. At the end of the after-stirring, the pH of the reaction mixture was 9.7. The reaction mixture was subsequently admixed at 25° C. with 25 g of HCl solution (32% strength by weight aqueous solution), and the complete solution was heated to 55 to 60° C. and then adjusted to a pH of 1.5 to 3 using 100 g of HCl solution (32% strength by weight aqueous solution). The reaction mixture was cooled to 20 to 25° C. and the solid was filtered off on a suction filter and washed ten times with 150 ml of water. The yield after drying under reduced pressure at 100° C. was 252.8 g (86.5% of theory). According to HPLC and NMR measurement, the product was free from decanoic acid and from unreacted para-hydroxybenzoic acid. The purity of the product is >99.9% by weight.

Example 13

Synthesis of Para-decanoyloxybenzoic Acid (DOBA)

798.3 g (5.78 mol) of para-hydroxybenzoic acid were first dissolved in 1980 ml of water and 2970 ml of isopropanol and this solution was admixed at 10 to 15° C. with 1329.7 g of KOH solution (50% strength by weight aqueous solution, 11.84 mol). The resulting pH was 14. Metered into this solution over the course of 100 minutes, then, at 10 to 15° C. were 1106.8 g (5.78 mol) of decanoyl chloride (99.6% strength by weight solution), and the batch was stirred for 15 minutes at 10 to 15° C. thereafter. The reaction mixture was subsequently admixed at 10 to 15° C. with 149.1 g of HCl solution (31% strength by weight aqueous solution), and the complete solution was heated to 65 to 70° C. and then adjusted to a pH of 1.5 to 3 using 596.5 g of HCl solution (31% strength by weight aqueous solution). The reaction mixture was cooled to 20 to 25° C. and the solid was filtered off on a suction filter and washed ten times with 750 ml of water. The yield after drying under reduced pressure at 100° C. was 1487 g (88% of theory). According to HPLC and NMR measurement, the product was free from decanoic acid and from unreacted para-hydroxybenzoic acid. The purity of the product is >99.9% by weight.

The invention claimed is:

1. A process for preparing an acyloxybenzoic acid of the formula (I)

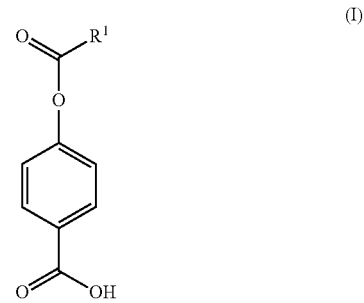

wherein
$R^1$ is a linear or branched, saturated alkyl group having 6 to 30 carbon atoms, a linear or branched, singly or multiply unsaturated alkenyl group having 6 to 30 carbon atoms, or an aryl group having 6 to 30 carbon atoms,
comprising the steps of
a) admixing para-hydroxybenzoic acid, in a solvent mixture comprising water and at least one organic solvent, with an alkali metal hydroxide, in an alkali metal hydroxide : para-hydroxybenzoic acid molar ratio ≥1.9:1 and only thereafter adding a carboxylic halide of formula $R^1$COHal, in which $R^1$ is defined above and Hal is a halide, at a temperature ≤25° C., and carrying out reaction,
b) adjusting the reaction mixture after step a), at a temperature ≤25° C., to a pH of 6 to 8.5 by addition of acid, if the pH at the end of step a) is not already within this range, c) subsequently heating the reaction mixture to a temperature of 35 to 80° C. and thereafter adjusting it to a pH of 1 to 4 by addition of acid, and e) adding the entire amount of alkali metal hydroxide in step a) before the addition of the carboxylic halide to the reaction mixture, and otherwise adding no further base in the process.

2. The process as claimed in claim 1, wherein after step c) the reaction mixture is cooled to a temperature <35° C.

3. The process as claimed in claim 1, wherein the alkali metal hydroxide in step a) is KOH or NaOH.

4. The process as claimed in claim 3, wherein the alkali metal hydroxide in step a) is KOH.

5. The process as claimed in claim 1, wherein the at least one organic solvent in step a) is selected from the group consisting of linear or branched alcohols, open-chain ethers, or and cyclic ethers.

6. The process as claimed in claim 5, wherein the at least one organic solvent in step a) has from 1 to 10 carbon atoms.

7. The process as claimed in claim 6, wherein the at least one organic solvent in step a) is selected from the group consisting of methanol, ethanol, n-propanol, isopropanol, n-butanol, isobutanol, tert-butanol, diethyl ether, tetrahydrofuran, dioxane, and mixtures thereof.

8. The process as claimed in claim 7, wherein the organic solvent in step a) is isopropanol.

9. The process as claimed in claim 1, wherein the acid in step b) and in step c) has a pKa value of less than or equal to 4.0.

10. The process as claimed in claim 1, wherein the acid in step b) and in step c) is $H_2SO_4$ or HCl.

11. The process as claimed in claim 1, wherein the weight ratio of water to the at least one organic solvent in step a) is from 5:1 to 1:5.

12. The process as claimed in claim 1, wherein the weight ratio of water to para-hydroxybenzoic acid in step a) is from 2:1 to 10:1.

13. The process as claimed in claim 1, wherein $R^1$ is a linear or branched, saturated alkyl group having 6 to 30 carbon atoms, or a linear or branched, singly or multiply unsaturated alkenyl group having 6 to 30 carbon atoms.

14. The process as claimed in claim 13, wherein the radical $R^1$ is an alkyl group.

15. The process as claimed in claim 13, wherein a carboxylic acid, $R^1$—COOH from which the carboxylic halide $R^1$—COHal is derived is selected from the group consisting of octanoic acid, nonanoic acid, 3,3,5-isononanoic acid, decanoic acid and dodecanoic acid.

16. The process as claimed in claim 13, wherein the carboxylic acid from which the carboxylic halide $R^1$—COHal is derived is decanoic acid.

17. The process as claimed in claim 1, wherein the acyloxybenzoic acid produced is free from unreacted para-hydroxybenzoic acid.

18. The process as claimed in claim 1, wherein the acyloxybenzoic acid produced is free from acid of the formula $R^1COOH$.

19. The process as claimed in claim 1, wherein the reaction mixture is cooled to a temperature of from 5° C. to 25° C. after step c).

20. The process as claimed in claim 1, wherein step a) is carried out at a temperature of from 0° C. to 15° C.

* * * * *